United States Patent [19]

Miyata

[11] 4,294,241

[45] Oct. 13, 1981

[54] COLLAGEN SKIN DRESSING

[76] Inventor: Teruo Miyata, No. 314, 3-6-29, Shimoochiai, Shinjuku-ku, Tokyo, Japan

[21] Appl. No.: 86,547

[22] Filed: Oct. 19, 1979

Related U.S. Application Data

[63] Continuation-in-part of Ser. No. 805,003, Jun. 9, 1977, abandoned.

[51] Int. Cl.³ ............................................. A61L 15/00
[52] U.S. Cl. .................................... 128/156; 128/155; 128/DIG. 8
[58] Field of Search ............... 128/156, 155, 260, 296, 128/DIG. 8; 106/122, 155, 161; 260/117

[56] References Cited

U.S. PATENT DOCUMENTS

| | | | |
|---|---|---|---|
| 3,071,477 | 1/1963 | Klevens | 128/DIG. 8 |
| 3,939,831 | 2/1976 | Cioca et al. | 128/156 |
| 4,089,333 | 5/1978 | Utusuo et al. | 128/DIG. 8 |

*Primary Examiner*—Robert W. Michell
*Assistant Examiner*—T. J. Wallen
*Attorney, Agent, or Firm*—Edward J. Mahler

[57] ABSTRACT

Skin or wound dressings are prepared in gel or sheet form from enzyme-solubilized collagen and/or such chemically modified collagen. Improved sheet form dressing is prepared by tubular extrusion of such collagen gels.

8 Claims, No Drawings

COLLAGEN SKIN DRESSING

This application is a continuation-in-part of Ser. No. 805,003, filed June 9, 1977 now abandoned.

This invention relates to skin dressings consisting of collagen or chemically modified collagen in gel form, in porous sheet form or in semiporous film type form. The invention also relates to the production of such skin dressings by preparation of sterile succinylated collagen gel, and by preparation of collagen porous sheet made by successive processes of extrusion of collagen gel into coagulation bath, tanning with glutaraldehyde, and/or partial air-drying followed by freeze-drying. Bactericidal agents or antibiotics may be incorporated into the gel or sheet-type dressing.

At the present time numerous materials in such form as film, fabric, gauze, sponge and skin have been proposed as wound and burn dressings or as artificial skin and some have actually been used with varying degrees of success or lack thereof. Such materials include silicone products, polymers of the nylon type, polyesters, polypropylene, polyurethanes, cellulose, porcine skin, amnion, and various forms of collagen itself.

A number of investigators including the present inventor and his colleagues have suggested the use of collagen material as a skin, burn or would dressing. The feature of this invention, however, consists in the form of the collagen dressing and in the method of producing such desired types.

The National Fire Protection Association reported in 1962 that approximately 1,800,000 persons sustain burns yearly and occupy over 11,000 hospital beds per day. There is a great need for a readily available, easily stored and temporary substitute for human skin for the effective treatment of thermal burns and other forms of skin loss. It is common practice to cover skin loss area with split-thickness autografts, homografts and heterografts. Such treatments protect against infection, and the loss of protein fluid and electrolytes from exposed tissue. These treatments, however, have the following drawbacks. Grafts are difficult to obtain, and to store for any prolonged period of time and also are quite expensive. These difficulties could be reduced by the development of artificial skin dressings which are inexpensive and readily available to use.

Collagen is a major protein of connective tissue such as skin, cornea, etc. and can be solubilized, separated and purified by treatment with proteolytic enzymes (other than collagenase), e.g., proctase, pepsin, trypsin and pronase. Enzyme-solubilized collagen is telopeptides-poor (atelocollagen), reltively inexpensive and ideal as a material for development into a skin wound dressing. It is superior in antigenic properties due to removal by the enzyme of telopeptides, etc. and is readily accepted by the human body.

Solubilized collagen has many $NH_2$ and $COOH$ groups in its structure, and chemical modifications of the molecule can be readily made, e.g., all or some of the amino groups may be acylated by reaction with a mixture of acetic anhydride and acetic acid. Similarly, succinic anhydride reacts with collagen replacing amino groups by carboxyl groups. The carboxyl groups contained in the molecule are susceptible to esterification by the standard reaction with acidified alcohol, e.g., reaction with anhydrous methanol acidified with HCl. In the above reactions the net isoelectric point of collagen can be controlled, either negative or positive, or completely neutralized.

Atelocollagen and chemically modified forms thereof may be employed in the practice of this invention, e.g., esterified collagen (alkaline isoelectric point) and modified amino-group forms, e.g., anhydride derivatives (acidic isoelectric point). In the preparation of gel type dressings of this invention the use of anhydride derivatives of atelocollagen (acidic isoelectric point), e.g., succinic anhydride derivatives of atelocollagen is preferred.

Gel Type

The gel type skin dressings of this invention are especially suitable for application to irregular body surfaces, e.g., areas of the joints, elbows, knees, etc. The gel dressing is preferably used in the form of a viscous paste of petroleum jelly consistency and contains 1–10%, preferably 2–5% of collagen.

In the preparation of the collagen gel, cleaned, dehaired hide or skin is cut into pieces of workable size and slurried in acidified water in the presence of a proteolytic enzyme (other than collagenase). Suitable enzymes are pepsin, trypsin, pronase, proctase, etc. Two fractions are obtained from this digestion, one an insoluble solid fraction which is discarded, and a solution or soluble fraction which is worked up as follows. The solution is brought to a pH of about 10.0 to denature the remaining active enzyme, and then acidified to a pH of about 6.0–7.0. Atelocollagen precipitates at this pH, leaving behind in solution (to be discarded) the digested telopeptides, and other contaminating proteins, and any saccharides, mucopolysaccharides, etc. The atelocollagen is usually further purified by repeated solubilization at pH 2.0–5.0 and reprecipitation at pH of 6.0–7.0, and recovered as a viscous solid usually by cheesecloth filtering. It is then air-dried, and subsequently converted to gel by solution in acidified water at a pH of about 3.0.

Succinylated atelocollagen was preferably used for making viscous gel skin dressing since it can be redissolved in water at physiologic pH (6.8–7.4) without requiring dialysis against water to remove acid during its preparation. Collagen concentration of gel skin dressing was between 0.5% to 7% and into it was incorporated the following bactericidal agents: silver nitrate solution (0.5 g/100 ml) or silver lactate solution (0.5 g/100 ml) 25 mg/ml Lincomycin, 5 mg/ml Amphotericin B and 25 mg/ml Gentamicin, or one or more thereof. The above gel is preferably retained substantially in the monomer state. No tanning or cross-linking is applied thereto.

Porous Sheet Type

Another type of collagen skin dressing (porous sheet) was prepared as follows: Enzyme-solubilized collagen gel (pH 2.0–3.5, collagen concentration 1%–10%) prepared as recited above was extruded from a tubular nozzle into a coagulation bath (saturated NaCl). Coagulated tubular collagen was cut longitudinally to obtain sheet and tanned with 1–5% glutaraldehyde in saturated NaCl containing 0.05 M $Na_2HPO_4$ (pH 8.7) for 0.5–3.0 hours. The tanned collagen sheet was washed with water repeatedly, then freeze-dried on a methylmethacrylate plate. To produce a semi-porous, film type sheet in which the upper surface of the sheet is more concentrated in collagen (resulting in an upper film type surface) and in which the lower surface of the sheet is less concentrated in collagen (i.e. more porous and sponge-like) the sheet is subject to partial air-drying prior to freeze-drying. Collagen sheet was sterilized by ethylene oxide gas and soaked in a typical base solution containing one or more bactericidial agents, such as silver nitrate (0.5 g/100 ml), or silver lactate (0.5 g/100 ml), or lactated Ringer's solution containing 25 mg/ml Gentamicin, 25 mg/ml Lincomycin, 25 mg/ml Colistimethate, 25 mg/ml Kanamycin, and 5 mg/ml Amphotericin B; or lactated Ringer's solution containing 25 mg/ml Lincomycin, 5 mg/ml Amphotericin B, and 25 mg/ml Gentamicin.

When viscous gel is extruded through an appropriate circular nozzle into a saturated salt bath the gel becomes dehydrated and the collagen becomes highly concentrated via coagulation. The collagen emerges from the coagulation bath in tubular form. Upon longitudinal slitting of the tube the collagen is converted to a flat-surfaced article the width and thickness of which is determined substantially by the dimensions of the extrusion nozzle. Tubular extrusion for the preparation of the collagen membrane sheet has distinct advantages over the filament type of extrusion, e.g., that disclosed by Utsuo et al (U.S. Pat. No. 4,089,333). The preparation of filamemt-type collagen dressing is complicated. First, spun collagen fiber must be prepared from collagen gel by extrusion, dried, tanned, washed and cut into staple. Non-woven fabric is then prepared from the staple on a webbing machine followed by dipping into a binder solution and drying. In comparison, the tubular extrusion method employed in applicant's invention is relatively simple. In addition, the filament-type dressing of Utsuo is too loose in its physical structure to prevent body fluid loss which is one of the prime requisites for a burn or wound dressing. On the other hand tubular extruded collagen sheet has a tighter physical structure (basically less porous). The porosity of the extruded sheet can be changed or controlled by altering the water content of the sheet; the higher the water content the higher the degree of porosity.

An effective skin dressing should have the following properties:
1. good adherence to wound surface, and acceleration of epitheliazation,
2. prevention of loss of protein, fluid and electrolytes,
3. prevention of infection,
4. reduction of pain,
5. long term preservation capability,
6. no stimulation of local tissue response, etc.

Collagen skin dressings described here satisfy the above properties and are easy to use, readily available and less expensive. Gel skin dressing is especially suitable for application to irregular surfaces, e.g., joint surfaces. Viscous gel-like paste and gels of petroleum jelly consistency show excellent adherence to the wound. Extensive cell ingrowth into the porous collagen sheet was observed. All skin dressings indicated effective protection against infection and good wound healing.

The present invention may be further understood from the following examples:

EXAMPLE 1

Fresh calfskin (about 5 kg) was dehaired, cleaned by shaving and cut into small pieces. The skin was washed repeatedly with 10% NaCl containing a 0.2% sodium azide bactericide and with sterilized water. The skin was solubilized in 10 liters of water (pH 2.5 HCl) containing 30 mg/ml Gentamicin by addition of 1 g. of pepsin (approximate ratio of enzyme to collagen was 1/400) at 20° C. for 4 days with intermittent stirring. The resulting viscous solubilized collagen was filtered through cheesecloth, its pH raised to 10 by NaOH and allowed to stand for 24 hours at 20° C. to inactivate the pepsin. The pH of collagen was then adjusted to 7-8 (HCl) and collagen precipitate was collected by centrifuging and washed with sterilized water. The washed precipitate was redissolved in acidic solution and re-precipitated at pH 7-8 for further purification.

Succinylation of solubilized collagen was performed as follows: Ten grams (dry basis) of solubilized collagen precipitate was resuspended in 4 liters of water and its pH adjusted to 9.0 by NaOH. Acetone solution (100 ml) containing 2.0 g. of succinic anhydride was gradually added to the collagen suspension. During the addition of succinic anhydride the pH of collagen suspension was maintained at about 9.0 NaOH solution. Succinylated collagen was precipitated by acidification to about pH 4.2, washed with water and freeze-dried. This freeze-dried collagen (sponge-like in form) was sterilized to remove micro-organisms. Five grams of the sterilized collagen sponge was dissolved in acidified water. Upon addition of NaOH to a pH of about 7.4 the collagen emerges in a highly viscous form. It was preserved by addition of silver nitrate (0.5% solution). This gel skin dressing was excellent in adhesion to the wound, in wound healing, and in protection against infection.

EXAMPLE 2

Succinylated solubilized collagen was prepared by the method described in Example 1. Sterilized succinylated collagen (10 g) was treated in the same manner as in Example 1 but preserved by silver lactate (0.5% solution). This gel skin dressing again displayed excellent properties as above.

EXAMPLE 3

Sterilized succinylated collagen was prepared by the method described in Example 1 and treated in the same manner as in Example 1 but was preserved in sterile lactated Ringer's solution (0.6% NaCl, 0:31% sodium lactate, 0.03% potassium chloride, 0.02% calcium chloride, pH adjusted to 7.4) containing the following antibiotics: 25 mg/ml Lincomycin, 5 mg/ml Amphotericin B, and 25 mg/ml Gentamicin. This gel skin dressing once again displayed excellent properties.

EXAMPLE 4

Solubilized collagen (not succinylated) was prepared by the method described in Example 1. The collagen was dissolved in dilute HCl solution (final pH 2.5, collagen concentration was 3%) and deairated under vacuum. Collagen acidic gel was extruded into a coagulation bath (saturated NaCl) through an appropriate tubular nozzle. Coagulated tubing was recovered, cut longitudinally and made into sheets and tanned with 3% glutaraldehyde in saturated NaCl containing 0.05 M $Na_2HPO_4$ for one hour. After repeated washing with water, collagen sheet was freeze-dried on a methylmethacrylate plate. Freeze-dried sheets (10 cm × 10 cm) were sterilized by treatment with ethylene oxide gas and preserved by soaking in 0.5% silver nitrate solution. Final thickness of the sheet was 3 mm. This skin dressing was excellent in the adhesion to the wound, in protection against fluid loss and infection, and in wound healing.

EXAMPLE 5

Collagen sheet was prepared by extrusion, tanning and washing by the method described in Example 4, except using 5% acidic collagen gel. Washed collagen sheet was then partially air-dried on a methylmethacrylate plate until the thickness of the sheet became half of the original. This partial drying reduces the porosity (collagen concentration higher) of the upper surface of the sheet. It was then freeze-dried to render the lower surface porous (collagen concentration lower), and sterilized with ethylene oxide gas. Sterilized sheet was preserved in sterile 0.5% silver lactate solution (pH 7.4). The final thickness of the sheet was 2 mm. This skin dressing had finer porosity and greater strength than the sheet of Example 4. It was excellent in protection of protein, fluid and electrolytes loss, in protection against infection and in wound healing.

EXAMPLE 6

Sterile, freeze-dried collagen sheet was prepared by the method described in Example 4, except that the collagen concentration was 5%. The sheet was preserved by soaking in sterile lactated Ringer's solution (pH adjusted to 7.4) containing the following antibiotics: 25 mg/ml Gentamicin, 25 mg/ml Lincomycin, 15 mg/ml Colistimethate, 25 mg/ml Kanamycin and 5 mg/ml Amphotericin B. The final thickness of the sheet was 4 mm. This sheet likewise displayed excellent skin dressing properties.

Although the tanning of the atelocollagen has been exemplified by glutaraldehyde treatment other aldehydes such as formalin and acrolein may be used. The extruded collagen may be treated in the tanning process while in tubular form or in flat sheet form. Tanning of the sheet form by means of the standard ultraviolet exposure is quite effective. Chromic acid treatment accomplished similar satisfactory cross-linking.

The following are results of experimental and clinical studies of tubular extruded atelocollagen sheet prepared by the process of this invention and conducted in Japan at a prominent biomaterial research center and at a children's medical center.

The skin of rabbit's back was removed with dermatorm in a thickness of 10/1000, 15/1000 and 20/1000 inches, and the wounds were covered with atelocollagen sponge sheet. Histological evaluation was carried out periodically but it was seen that collagen sponge produced brown scab. Blood penetrated into collagen sponge and coagulated to form a scab. The wound of 10/1000 inches in depth was almost completely healed in 7 days after covering with the collagen sponge. Cell infiltration mainly consisting of eosino-leukocyte was seen between the collagen sponge sheet and upper dermis in the wound of 15/1000 inches in depth in 4 days after collagen covering. In the wound of 20/1000 inches in depth, cell infiltration extended into the collagen sponge sheet, and unification of collagen sponge and inflammatory layer was seen in 7 days after collagen covering. In fourteen days on the same rabbit it was seen that the number of eosino-leukocytes decreased and fibroblast increased. These observations are very similar to those when aminion was used as a dressing.

In the case of application of collagen sponge sheet to de-epithelialized area (6/1000 inches in thickness) of a 5 year old male, blood penetration to the sponge sheet surface was seen within 7 days and the collagen sponge was automatically falling off after epithelization within 15 days. On the other hand, another half of the wound covered by Sofratulle gauze was epithelialized 4–5 days later than the epithelization of the wound covered by collagen sponge sheet.

In the case of a collagen sponge sheet covering the de-epithelialized area (6/1000 inches in thickness) of the waist of a 5-year old male, the wound dried in several days and was completely healed in 17 days.

In another case of the use of collagen sponge sheet to a small leg burn wound (applied one month after injury), the wound was contracted effectively in 4 days after collagen sheet application and the epithelization was completed several days after the wound contraction.

Having described the invention so that it may be practiced by those skilled in the art:

What is claimed is:

1. A method for the preparation of a collagen skin dressing in sheet form which comprises the steps of:
   (a) treating a source of collagen with a proteolytic enzyme to form a telopeptide-poor, monomolecularly dispersed atelocollagen extract,
   (b) precipitating atelocollagen from the extract,
   (c) purifying the precipitated atelocollagen by redissolving and re-precipitation,
   (d) converting the extracted, purfied atelocollagen to a gel,
   (e) extruding the atelocollagen gel through a circular extrusion nozzle in a coagulation bath,
   (f) recovering atelocollagen in tubular form from the coagulation bath,
   (g) slitting the tubular collagen longitudinally to form a collagen sheet therefrom,
   (h) cross-linking the longitudinal sheet, and
   (i) subjecting the cross-linked sheet to freeze-drying.

2. A method according to claim 1 in which the cross-linking is carried out by tanning with glutaraldehyde.

3. A method according to claim 1 in which there is incorporated into the atelocollagen sheet at least one substance selected from the group consisting of antibiotics and bactericides.

4. Collagen skin dressing prepared by the method of claim 1.

5. A method for the preparation of a collagen skin dressing in sheet form whose upper and lower surfaces possess differing porosity characteristics which comprises the steps of:
   (a) treating a source of collagen with a proteolytic enzyme to form a telopeptide-poor, monomolecularly dispersed atelocollagen extract,
   (b) precipitating atelocollagen from the extract,
   (c) purifying the precipitated atelocollagen by redissolving and reprecipitation,
   (d) converting the extracted, purified atelocollagen to a gel,
   (e) extruding the atelocollagen gel through a circular extrusion nozzle in a coagulation bath,
   (f) recovering atelocollagen in tubular form from the coagulation bath,
   (g) slitting the tubular collagen longitudinally to form a collagen sheet therefrom,
   (h) cross-linking the longitudinal sheet,
   (i) partially air-drying the cross-linked sheet, and
   (j) freeze-drying the partially air-dried sheet whereby the upper surface of said sheet becomes more concentrated in atelocollagen content with the lower surface thereof.

6. The method of claim 5 in which the cross-linking is accomplished by exposing the atelocollagen sheet to ultraviolet light.

7. The method of claim 5 in which there is incorporated into the sheet dressing at least one substance selected from the group consisting of antibiotics and bactericides.

8. Collagen skin dressing prepared by the method of claim 5.

* * * * *